(12) United States Patent
King et al.

(10) Patent No.: US 12,004,941 B2
(45) Date of Patent: Jun. 11, 2024

(54) STENT-GRAFT

(71) Applicant: Cook Medical Technologies LLC, Bloomington, IN (US)

(72) Inventors: Chantelle King, Queensland (AU); Ryan Bradway, Temecula, CA (US); Jarin Kratzberg, West Lafayette, IN (US); Kevin Wilger, Lafayette, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 58 days.

(21) Appl. No.: 17/744,960

(22) Filed: May 16, 2022

(65) Prior Publication Data

US 2022/0273417 A1 Sep. 1, 2022

Related U.S. Application Data

(63) Continuation of application No. 16/536,854, filed on Aug. 9, 2019, now Pat. No. 11,331,178.
(Continued)

(30) Foreign Application Priority Data

Aug. 9, 2018 (AU) ................. 2018214103

(51) Int. Cl.
*A61F 2/07* (2013.01)
*A61F 2/89* (2013.01)
(Continued)

(52) U.S. Cl.
CPC .................. *A61F 2/07* (2013.01); *A61F 2/89* (2013.01); *A61F 2/91* (2013.01);
(Continued)

(58) Field of Classification Search
CPC ...... A61F 2/00; A61F 2/89; A61F 2/91; A61F 2002/075; A61F 2002/91583; A61F 2220/0075
See application file for complete search history.

(56) References Cited

U.S. PATENT DOCUMENTS

| 4,902,508 A | 2/1990 | Radylak et al. |
| 5,554,389 A | 9/1996 | Badylak et al. |

(Continued)

OTHER PUBLICATIONS

Extended European Search Report for EP Application No. 19191099.1 dated Apr. 9, 2020, 9 pages.

*Primary Examiner* — Suba Ganesan
(74) *Attorney, Agent, or Firm* — Crowell & Moring LLP

(57) ABSTRACT

A stent-graft comprises: a graft defining an elongate lumen having a longitudinal axis; an external stent having a plurality of struts and apices between the struts, the apices including proximal apices and distal apices; a set of proximal sutured knots, the proximal sutured knots securing the proximal apices of the stent to the graft; a set of distal sutured knots, the distal sutured knots securing the distal apices of the stent to the graft; and a plurality of intermediate sutured knots, formed along a continuous suture, the continuous suture including a plurality of bridging portions, the bridging portions bridging between neighbouring struts of the stent, the intermediate sutured knots securing struts of the stent to the graft.

20 Claims, 13 Drawing Sheets

Related U.S. Application Data

(60) Provisional application No. 62/716,444, filed on Aug. 9, 2018.

(51) Int. Cl.
*A61F 2/91* (2013.01)
*A61F 2/915* (2013.01)

(52) U.S. Cl.
CPC .................. *A61F 2002/075* (2013.01); *A61F 2002/91583* (2013.01); *A61F 2220/0075* (2013.01)

(56) References Cited

U.S. PATENT DOCUMENTS

| | | |
|---|---|---|
| 5,993,844 A | 11/1999 | Abraham et al. |
| 6,039,758 A | 3/2000 | Quiachon |
| 6,099,567 A | 8/2000 | Badylak et al. |
| 6,206,931 B1 | 3/2001 | Cook et al. |
| 7,399,314 B2 | 7/2008 | Butaric et al. |
| 7,407,509 B2 | 8/2008 | Greenberg et al. |
| 8,348,988 B2 | 1/2013 | Lad et al. |
| 8,690,937 B2 | 4/2014 | Majercak |
| 8,702,787 B2 | 4/2014 | Arbefeuille |
| 9,855,155 B2 | 1/2018 | Majercak |
| 2005/0159803 A1* | 7/2005 | Lad .......................... A61F 2/07 623/1.13 |
| 2005/0159804 A1 | 7/2005 | Lad et al. |
| 2009/0149939 A1 | 6/2009 | Godlewswki et al. |
| 2009/0171451 A1 | 7/2009 | Kuppurathanam et al. |
| 2011/0071614 A1 | 3/2011 | Majercak et al. |
| 2011/0270378 A1 | 11/2011 | Bruszewski et al. |
| 2013/0306232 A1 | 11/2013 | Hedberg et al. |
| 2016/0235517 A1 | 8/2016 | Sethna et al. |
| 2016/0270935 A1 | 9/2016 | Rasmussen |
| 2018/0116783 A1 | 5/2018 | Kratzberg et al. |

\* cited by examiner

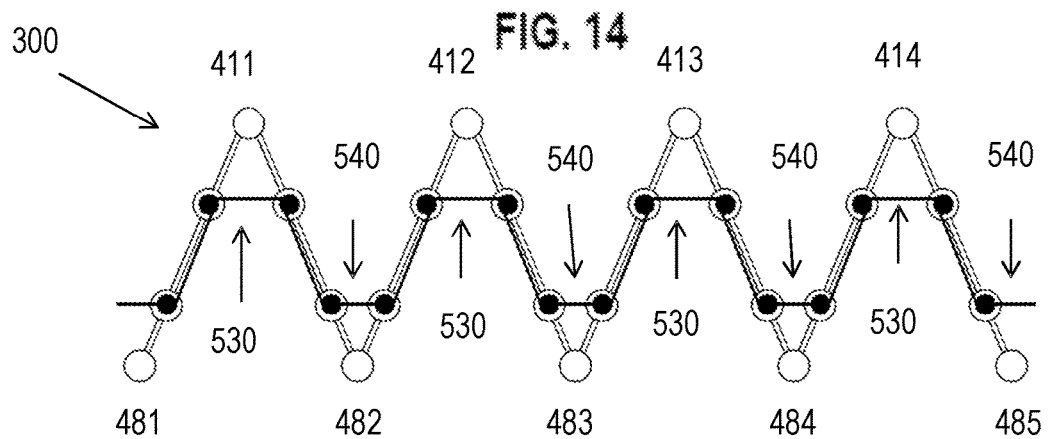
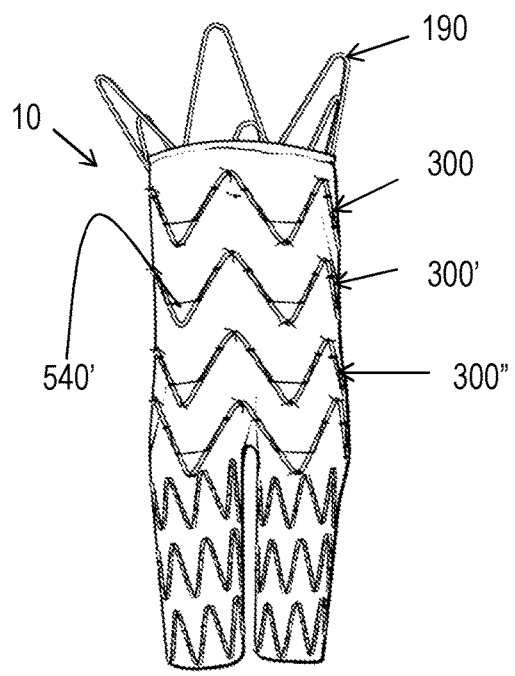
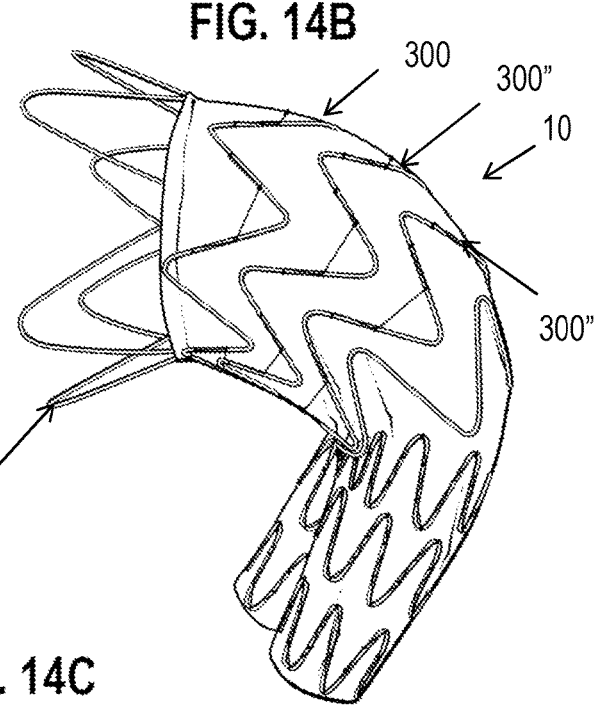
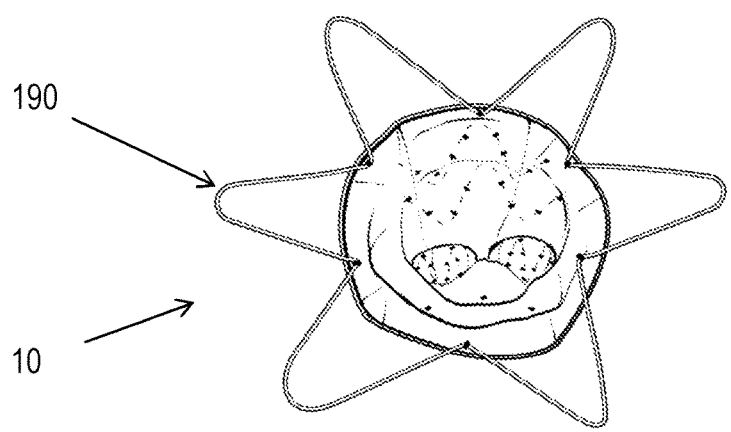

STENT-GRAFT

RELATED APPLICATIONS

The application is a continuation of U.S. patent application Ser. No. 16/536,854, filed Aug. 9, 2019, which claims the benefit of the filing date under 35 U.S.C. § 119(e) of Provisional U.S. Patent Application Ser. No. 62/716,444, filed Aug. 9, 2018, and also claims priority to Australian Patent Application No. 2018214103, filed on Aug. 9, 2018, issued as Patent No. 2018214103 on Jan. 17, 2019, which are hereby incorporated by reference in their entireties.

BACKGROUND

1. Technical Field

The present invention relates generally to the field of medical devices. Particular embodiments are related to medical devices that are deployable into bodily lumens including vascular systems, and especially to stent-grafts and their manufacture.

2. Background

Stents grafts for insertion into a body passageway, such as a vascular passageway or other body lumen are used in situations where the passageway or lumen may have a defect, such as a stenosis or an aneurysm. Stents perform functions that make them useful in combination with grafts. A stent can resist pressure on a graft, and help to provide support for a blood vessel. A stent can provide an outward pressure to keep the graft and hence the lumen open. A stent can also be self-expanding so as to deploy a stent-graft from a compressed and radially compact condition to an expanded deployed condition. A stent may also be used to anchor the graft in place, where anchors or barbs on the stent are provided. Such anchors can secure the stent, and hence the graft, in the desired location within a lumen of a patient.

Typically, stents are attached to grafts using sutures.

A difficulty with known stent-grafts is the complexity and assembly process time required for manufacture. Complexity introduces potential for mistakes.

A further issue with some known stent-grafts is bio-burden. That is, some stent-grafts are known to occasionally release suture material into a patient.

A yet further issue with some known stent-grafts is residual holes left in the graft after temporary or tacking stitches are removed.

BRIEF SUMMARY

The present invention seeks to provide an improved endoluminal prosthetic device or other medical device, such as a stent graft, and an improved method of forming an endoluminal prosthetic device.

According to an aspect of the invention, there is provided a stent-graft comprising:
  a graft having an elongate lumen and a longitudinal axis;
  at least one stent having a plurality of struts and an apex between each of the plurality of struts, the apices including proximal apices and distal apices;
  a running suture attaching the stent to the graft, the running suture comprising:
  first and second knots knotted along the length of each of at least some struts of the plurality of struts at intermediate points spaced from the proximal and distal apices of said at least some struts,
  a length of running suture running between the first and second knots, and
  a first bridging portion extending between a first knot on a first strut and a first knot on a second strut next adjacent the first strut, and a second bridging portion extending from a second knot on the second strut to a second knot of a third strut next adjacent the second strut.

Advantageously, the first bridging portion is proximal to the second bridging portion.

Preferably, the first bridging portion extends between two struts of a proximal apex and the second bridging portion extends between two struts of a distal apex.

The first bridging portion preferably extends between a first strut of a first proximal apex and a first strut of a second proximal apex.

A length of the bridging portions may pass in and out of the graft between next adjacent struts.

The stent graft may comprise a series of proximal tack knots securing the one or more of the proximal apices of the stent to the graft; and/or a series of distal tack knots securing one or more of the distal apices of the stent to the graft.

Preferably, the series of proximal and/or distal tack knots are configured such that the stent can slide relative to the graft.

The stent graft may comprise a third knot in the running suture between each of the first and second knots.

In the preferred embodiments, the bridging portions are disposed transverse to the longitudinal axis of the lumen.

Each strut of the plurality of struts advantageously has a first knot and a second knot and a first bridging portion extending from the first knot and a second bridging portion extending from the second knot.

It is preferred that the running suture is a single continuous length of suture.

According to another aspect of the present invention, there is provided a stent-graft comprising:
  a graft having an elongate lumen and a longitudinal axis;
  a plurality of discrete ring stents having a plurality of struts and apices between the struts, the apices including proximal apices and distal apices;
  a running suture attaching at least one stent of the plurality of stents to the graft, the running suture comprising:
  at least first and second knots knotted along the length of each strut at intermediate points on the struts away from the proximal and distal apices,
  a length of running suture running between the first and a second knots on each strut, and
  a first bridging portion extending between a first knot on a first strut adjacent a proximal apex and a first knot on a second strut adjacent the proximal apex, and a second bridging portion extending from a second knot on a second strut adjacent a distal apex to a second knot on a third strut adjacent the distal apex.

Advantageously, the first bridging portion and the second bridging portion are disposed transverse to the longitudinal axis of the lumen; and/or
  at least a portion of the first and second bridging portions passes through the graft; and/or
  the running suture is continuous about a circumference of the at least one stent; and/or
  each stent of the plurality of stents comprises a running suture having first and second knots and first and second bridging portions.

According to another aspect of the present invention, there is provided an aortic stent-graft comprising:
a graft having an elongate lumen and a longitudinal axis;
an external zig zag stent having a plurality of struts and apices between the struts, the apices including proximal apices and distal apices, the stent extending around an external circumference of the graft;
a set of removable proximal sutured knots, the proximal sutured knots securing the proximal apices of the stent to the graft;
a set of removable distal sutured knots, the distal sutured knots securing the distal apices of the stent to the graft; and
a plurality of intermediate sutured knots separate from the set of removable proximal and distal knots, formed along a running suture, the running suture including a plurality of bridging portions, the bridging portions disposed transverse to the longitudinal axis of the lumen and bridging between adjacent struts of the stent, the intermediate sutured knots securing struts of the stent to the graft.

Advantageously, the plurality of bridging portions passes into and out of the graft between adjacent struts of the external zig zag stent and/or the running suture is continuous about a circumference of the external zig zag stent.

According to an aspect of the invention, there is provided a stent-graft comprising:
a graft having an elongate lumen and a longitudinal axis;
an external stent having a plurality of struts and apices between the struts, the apices including proximal apices and distal apices;
a set of proximal sutured knots, the proximal sutured knots securing the proximal apices of the stent to the graft;
a set of distal sutured knots, the distal sutured knots securing the distal apices of the stent to the graft; and
a plurality of intermediate sutured knots, formed along a continuous suture, the continuous suture including a plurality of bridging portions, the bridging portions bridging between neighbouring struts of the stent, the intermediate sutured knots securing struts of the stent to the graft.

All aspects of the present invention, may have one or more of the following characteristics.

Advantageously, the bridging portions are disposed transverse to the longitudinal axis of the lumen.

The plurality of intermediate sutured knots along the continuous suture may include two or three intermediate sutured knots along each strut of the external stent.

The stent is may be zig zag stent. The stent is advantageously self expanding.

The zig zag stent preferably extends around an external circumference of the graft.

Advantageously, the proximal sutured knots and the distal sutured knots are locking knots.

The intermediate sutured knots may be over-threaded knots.

Preferably, the stent-graft is an aortic stent-graft.

The bridging portions may pass into and out of the graft such that they include external bridging portions and internal bridging portions.

Preferably, the stent-graft comprises a plurality of external stents disposed longitudinally along the graft, each stent having a plurality of struts and apices between the struts, the apices including proximal apices and distal apices thereby forming peaks and valleys, wherein adjacent stents are positioned such that peaks from one of the plurality of external stents extend towards or into valleys of another of the plurality of external stents.

Advantageously, the adjacent stents are positioned such that peaks from one of the plurality of external stents extend into valleys of another of the plurality of external stents.

According to another aspect of the invention, there is provided a method of forming an endoluminal prosthetic device, the method comprising the steps of:
providing a graft comprising a bio-compatible material and defining a main tubular body;
providing a first external stent comprising a plurality of struts and apices between the struts, the apices including proximal apices and distal apices;
positioning the first stent around the main tubular body;
joining the proximal apices and the distal apices of the first stent to the graft using respective sutured proximal knots and sutured distal knots;
joining the struts of the first stent to the graft by intermediate sutured knots in a continuous suture, the continuous suture bridging between neighbouring struts of the stent.

The step of joining the proximal and distal apices of the first stent to the graft may comprise joining using locking knots.

Advantageously, the step of joining the struts of the first stent to the graft by knots in a continuous suture comprises passing the continuous suture into and out of the graft so as to bridge between neighbouring struts of the stent.

The preferred embodiments will be particularly discussed in relation to stent-grafts for placement into the thoracic abdominal aorta or into the abdominal aorta for the treatment of aneurysms. The teachings herein are not, however, so restricted and may be applied to stent-grafts or any other medical device for placement in any lumen of the human or animal body.

the teachings herein can provide an improved stent graft, other medical device, and an improved method of forming an endoluminal medical device, while improving safety and simplifying assembly.

Other aspects and advantages of the teachings herein will become apparent to the skilled person having regard to the specific description that follows.

BRIEF DESCRIPTION OF THE DRAWINGS

Embodiments of the present invention are described below, by way of example only, with reference to the accompanying drawings, in which:

FIG. 14 is a schematic diagram of a suture stent fixation arrangement as taught herein;

FIGS. 14A to 14C show a stent graft having a sutured stent according to FIG. 14 will curve in use;

DETAILED DESCRIPTION OF THE DRAWINGS AND THE PRESENTLY PREFERRED EMBODIMENTS

Figure 1:
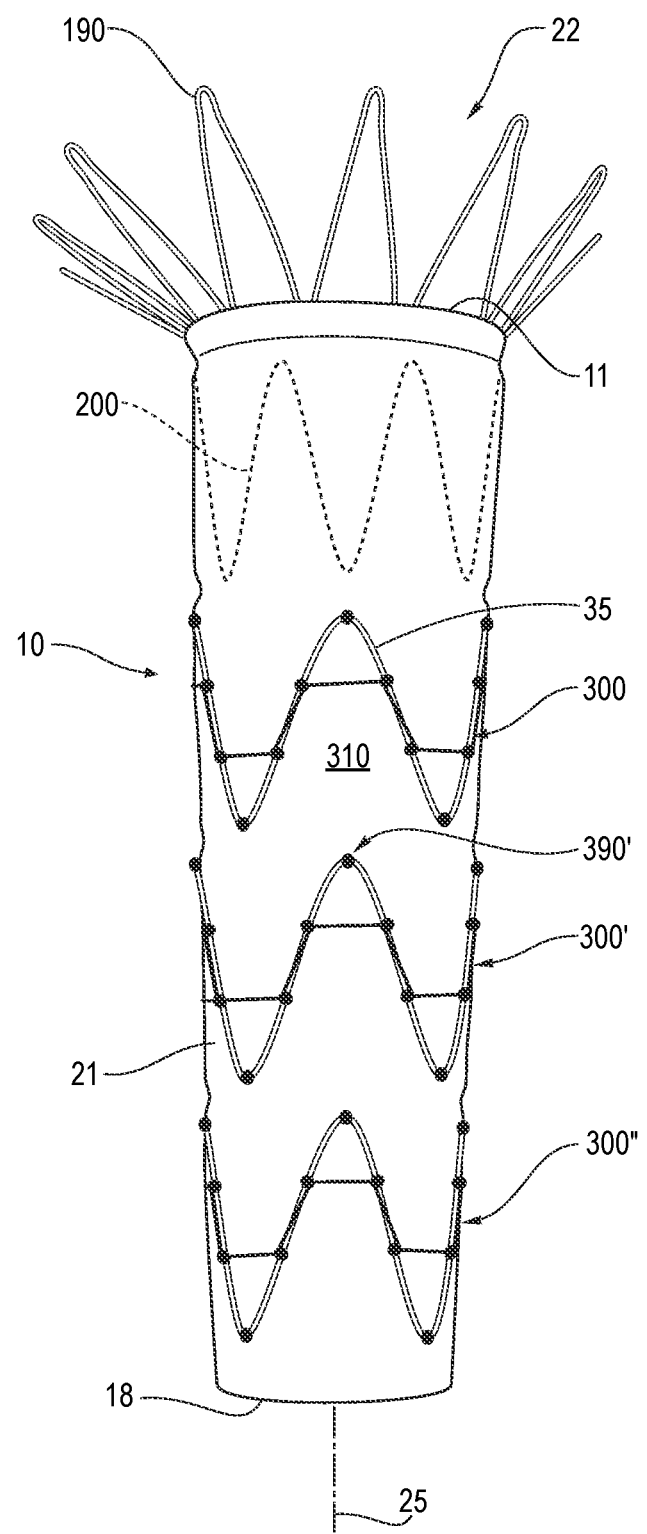
FIG. 1 is a diagrammatic isometric view of a stent-graft according to an embodiment of the invention.

For the purposes of understanding the principles of the teachings herein, reference will now be made to the embodiments illustrated in the drawings, and specific language will be used to describe them. It is to be understood that the Figures are, in some cases, schematic and do not show the various components in their actual scale. In many instances, the Figures show scaled up components to assist the reader.

Throughout this specification, the term "distal" with respect to a portion of the aorta, a deployment device or an endograft means the end of the aorta, deployment device or endograft further away in the direction of blood flow from the heart and the term "proximal" means the portion of the aorta deployment device or end of the endograft nearer to the heart in the direction of blood flow. When applied to other vessels, similar terms such as caudal and cranial should be understood.

Referring to FIG. 1, a stent-graft 10 having a proximal end 11 and a distal end 18 is shown. The stent-graft 10 comprises a graft 20 providing an elongate lumen 22 having a longitudinal axis 25 and one or more external stents 300. Now turning to FIG. 2, it can be seen that the external stent 300 has a plurality of struts 351, 352, 353, 354 and apices between the struts, the apices including proximal apices 311, 312, 313 and distal apices 381, 382.

In the embodiment of FIG. 1 the stent 300 is a zig zag stent and that the zig zag stent is self-expanding. In other embodiments of the invention, not shown, stents having different geometries may be used.

The zig zag stent 300 extends around an external circumference of the graft 20. Furthermore, it can be seen that there are a plurality of external stents disposed longitudinally along the graft, in this case three (3), each stent having a plurality of struts and apices between the struts. Typical examples of such struts and apices are shown more clearly in FIG. 2 as has been described above. The apices include proximal apices and distal apices thereby forming peaks and valleys, wherein adjacent stents are positioned such that peaks from one of the plurality of external stents extend towards or into valleys of another of the plurality of external stents. In FIG. 1 stent 300 forms a valley 310 into which peak 390' of stent 300' extends towards. In other embodiments adjacent struts are attached such that there is some overlap and where the peaks extend into valleys of and adjacent stent. Depending on requirements including flexibility, kink resistance, and preventing adjacent stents making metal to metal contact, positioning and overlap of adjacent stents can be varied. The term "valley" is intended to mean the V-shaped space between adjacent struts of a particular stent and applies irrespective of orientation (whether inverted or conventional orientation).

The stent-graft 10 shown in FIG. 1 is an aortic stent-graft. However, stent-grafts for other parts of an anatomy may also be provided according to the invention. With the aortic stent-graft 10 of FIG. 1, a terminal stent 190 is provided at a proximal end thereof. This terminal stent 190 may be provided with anchoring members in the form of barbs 195, such as those shown in FIG. 10. Such barbs 195 help decrease migration of the stent-graft 10 within the vessel in which it is deployed. The stent-graft 10 shown in FIG. 1 also includes an internal stent 200 and external stents 300, 300' and 300". Many other stent-graft configurations are possible and may incorporate the features of the teachings disclosed herein.

While the stents 300 are shown external to the graft tubing in these embodiments, it is to be understood that they may be disposed internally of the graft tubing, either all or one or more thereof.

Figure 3A:
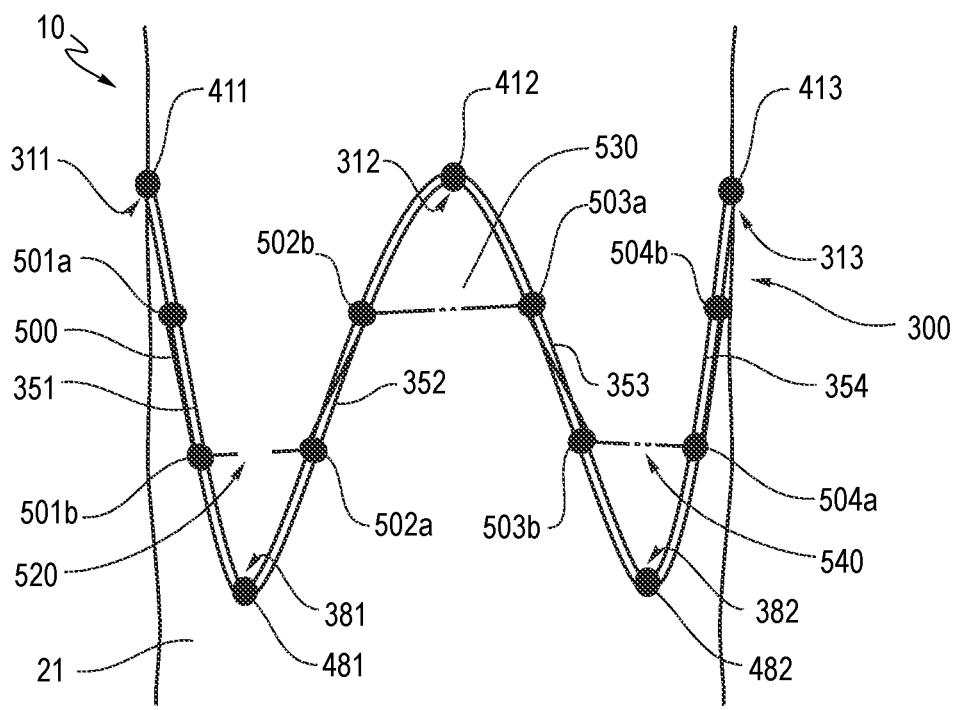
FIGS. 3A and 3B are a similar view to that of FIG. 2, showing a detailed view of a stent-graft according to another embodiment of the invention.

Now referring to FIG. 3A, it can be seen that the stent-graft comprises a set of proximal sutured knots 411, 412, 413, the proximal sutured knots securing the proximal apices 311, 312, 313 of the stent 300 to the graft 20. The stent-graft also comprises a set of distal sutured knots 481, 482, the distal sutured knots 481,482 securing the distal apices 381, 382 of the stent 300 to the graft 20. As explained in further detail below, the proximal and distal sutured knots 411-413 and 481-482 may in at least some embodiments be omitted, be removable or be loose sutures, allowing for the stent 300 to slide within the remaining sutures of the assembly.

A plurality of intermediate sutured knots 501a, 501b, 502a, 502b, 503a, 503b, 504a, 504b, formed along a continuous suture 500, are provided. The continuous suture 500 includes a plurality of bridging portions 520, 530, 540 bridging between neighbouring struts of the stent 300. The intermediate sutured knots secure the struts of the stent to the graft 20.

Figure 3B:
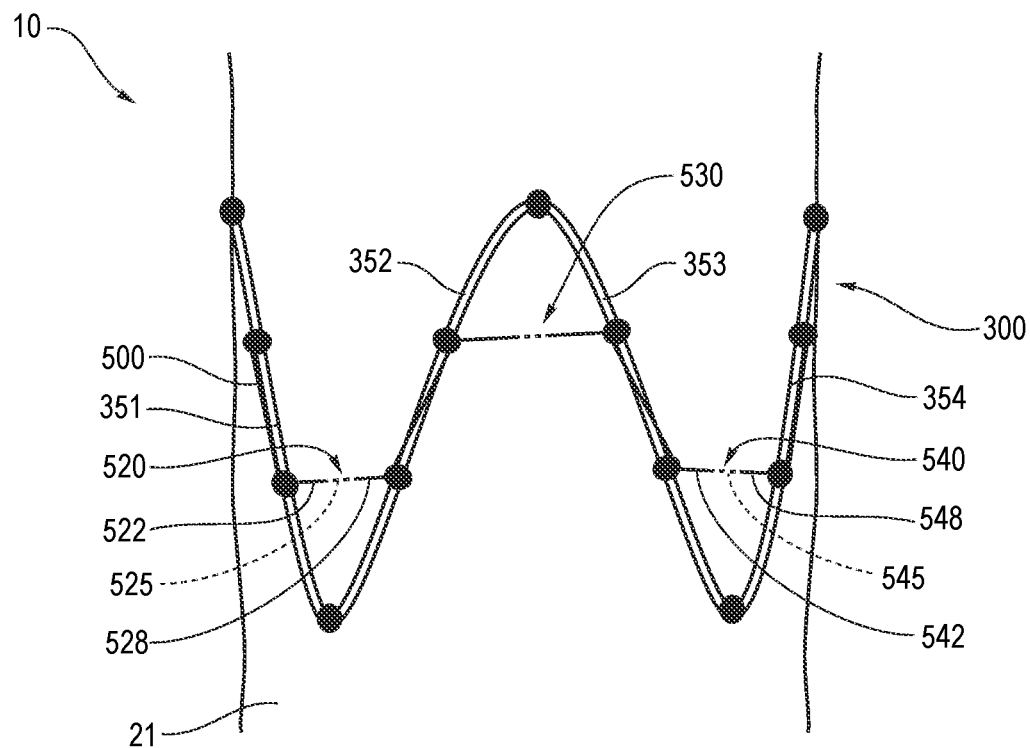

In the embodiment of FIGS. 3A and 3B, the bridging portions 520, 530, 540 pass into and out of the graft 20 such that they include external bridging portions such as 522 and 528 as shown in FIG. 3B, and internal bridging portions, such as 525 also shown in FIG. 3B.

With the embodiments shown in FIGS. 3A and 3B, where the suture has a path through the wall of the graft 20 into and out of the graft 20, so as to bridge between neighbouring struts of the stent, there is less risk of the suture 500 catching.

Looking at bridging portion 520 in FIGS. 3A and 3B, it can be seen that the bridging portion 520 bridges between knots 501b and 502a substantially circumferentially around a portion of the stent-graft between struts 351 and 352. The bridging portion 520 is disposed at almost exactly 90 degrees to the longitudinal axis 25 of the lumen (as shown in FIG. 1). In other embodiments, the angle at which the bridging portions are disposed transverse to the longitudinal axis of the lumen may vary. That is, they may be transverse at an angle other than 90 degrees, but still such that they bridge transversely across to the adjacent strut, rather than following along the strut and around its apex or point.

Figure 2:
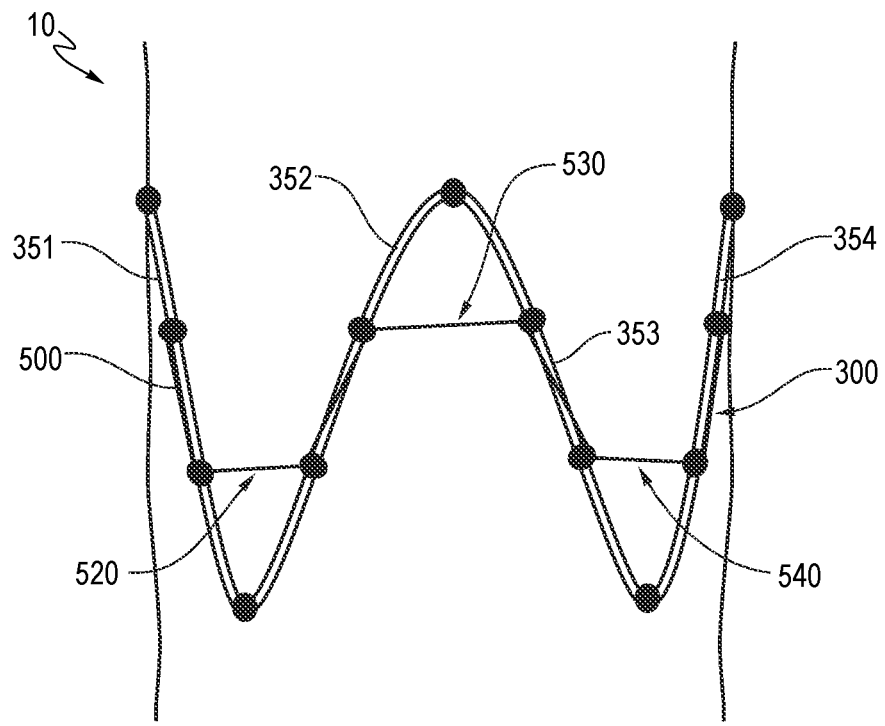
FIG. 2 is a detailed view of a portion of the stent-graft shown in FIG. 1.

When FIG. 1 is viewed together with FIG. 2, it can be seen that the bridging portions 520, 530, 540 are in this embodiment disposed transverse to the longitudinal axis 25 of the lumen 22.

Figure 4:
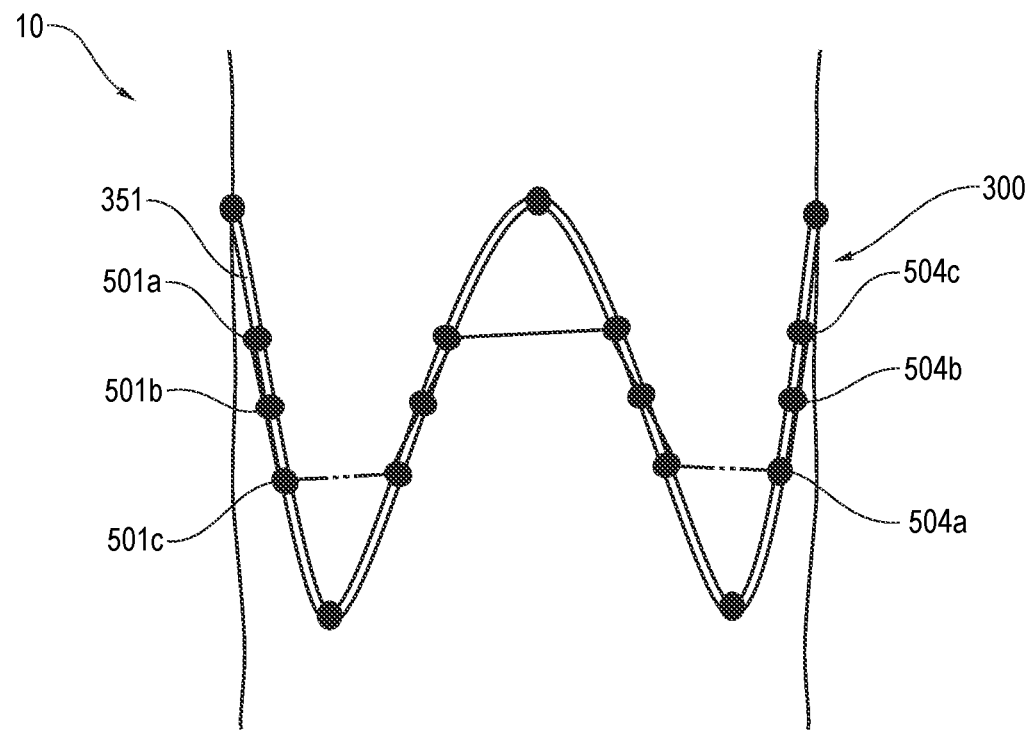
FIG. 4 is a similar view to that of FIG. 2, but shows a detailed view of a stent-graft according to another embodiment of the invention.

Again referring to FIGS. 1 and 2, it can be seen that the plurality of intermediate sutured knots along the continuous suture 500 include two intermediate sutured knots along each strut of the external stent 300. In contrast, in another embodiment of the invention shown in FIG. 4, there are three intermediate sutured knots along each strut of the external stent. For instance, FIG. 4 shows knots 501a, 501b and 501c along strut 351 of the external stent 300. In yet other embodiments (not shown), four or more intermediate sutured knots along each strut of the external stent may be provided depending on factors such as the size of the stent-graft. The intermediate sutured knots are preferably spaced evenly along their corresponding strut at 4 to 7 mm apart.

Figure 5:
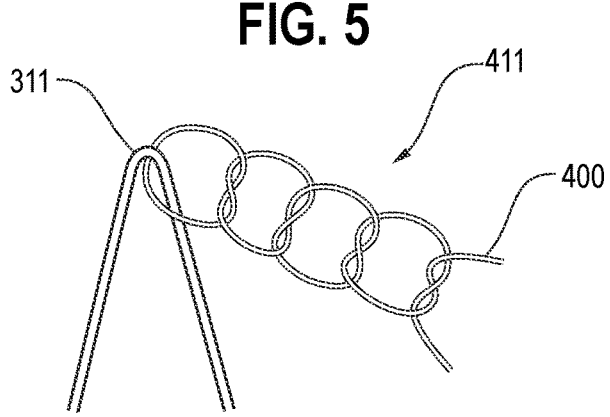
FIG. 5 is a detailed view showing a proximal apex of a stent and a proximal locking knot on a stent-graft according to embodiments of the invention.
Figure 6A:
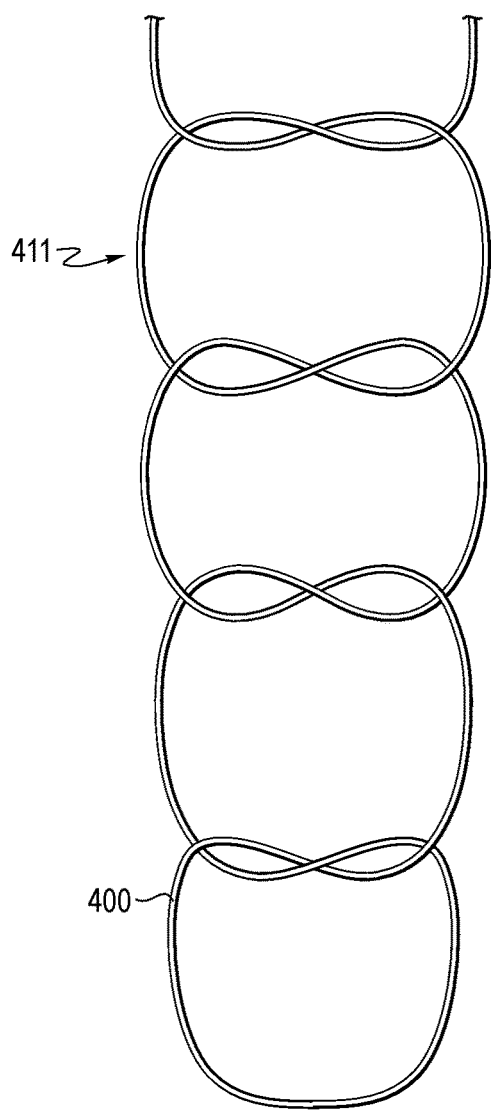
FIG. 6A is an annotated schematic diagram of the suture forming the locking knot of FIG. 5.

Now referring to FIG. 5, a proximal sutured knot 411 is shown in more detail. This proximal sutured knot 411 secures an apex 311 to the graft 20 with a locking knot formed by two pairs of double knots, sometimes referred to as reef knots. The proximal sutured knot 411 is a locking knot, as opposed to a tacking knot. It is a single stitch though the graft material, but has four knots (two pairs of double knots). The knots are a left over right knot, then a right over left knot, then a left over right knot and finally a right over left knot, as can be seen clearly in FIGS. 5 and 6A. Unlike with some prior art stent-grafts, this knot does not need to be removed.

Figure 6B:
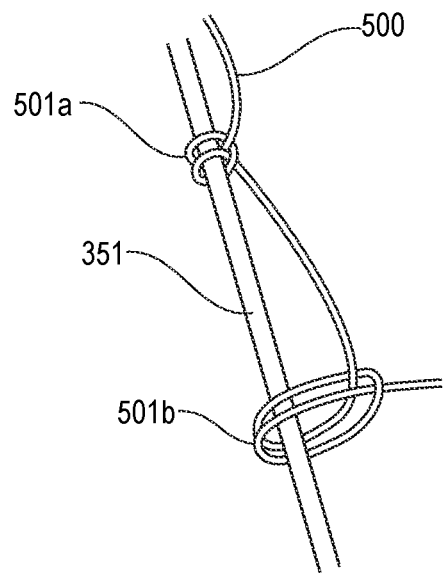
FIGS. 6B and 6C are detailed views of a strut of a stent on a stent-graft according to embodiments of the invention.
Figure 6C:
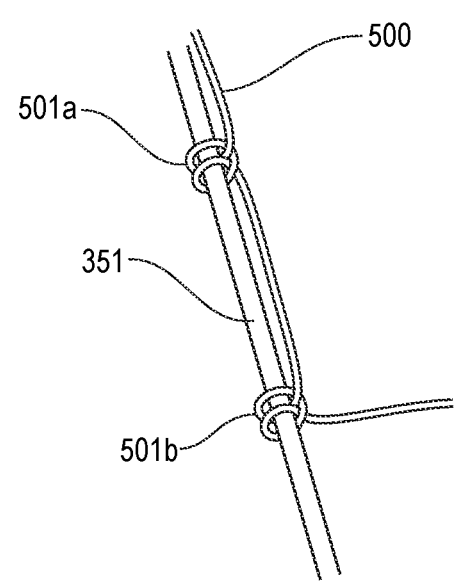
Figure 6D:
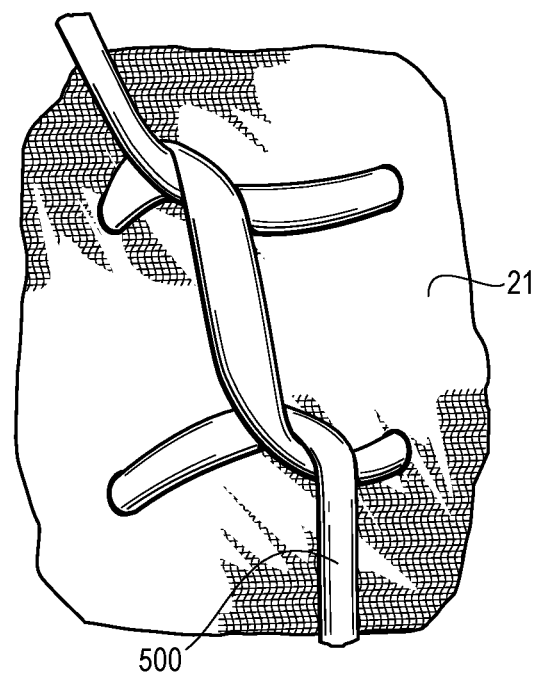
FIG. 6D is a view showing the tightened suture of the embodiment of FIGS. 6A to 6C.

FIGS. 6B and 6C show a portion of the continuous suture 500 along a strut in a magnified view. In FIG. 6B, a first intermediate knot 501a has been tied and a second intermediate knot 501b is in the first stage of being tied. In FIG. 6C, the second intermediate knot 501b is still partially tied ready for a second knot so that it will match the first intermediate knot 501a. FIG. 6D, shows the continuous suture 500 tied to a graft 21 and in particular the arrangement of the suture at the knots depicted in FIGS. 6B and 6C.

Figure 7A:
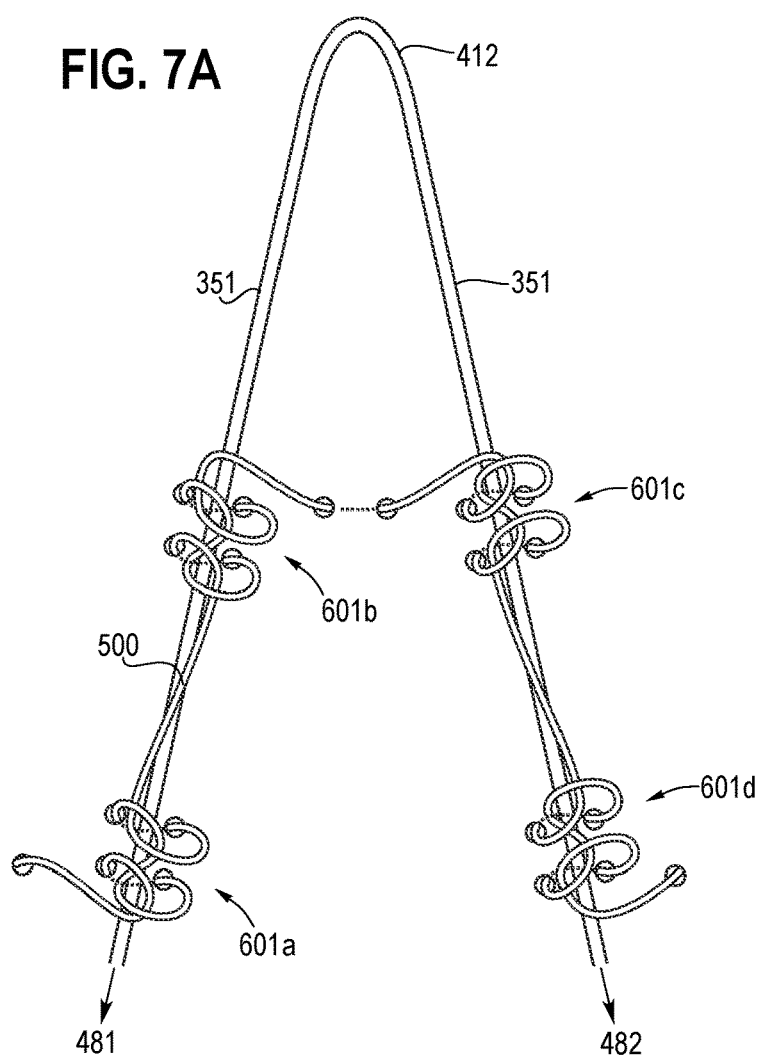
FIG. 7A is a detailed view of a strut of a stent on a stent-graft according to another embodiment of the invention.
Figure 7B:
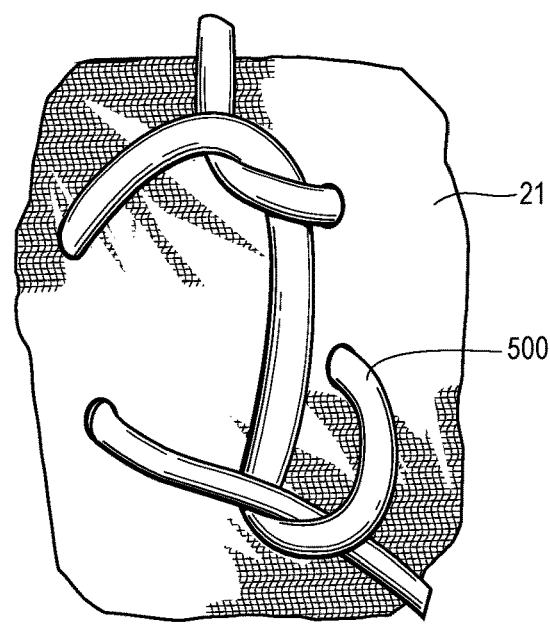
FIG. 7B is a view showing the tightened suture of the embodiment of FIG. 7A.

Referring now to FIGS. 7A and 7B, these show another embodiment of continuous suture with a modified knot arrangement compared to that of the embodiment of FIGS. 5 to 6D. In the embodiment of FIGS. 7A and 7B, four double knot arrangements 601a-601d are formed on the stent struts 351 intermediate the apices 412, 481, 482 of the stent. Each double knot of the continuous suture is effectively the same as the other knots 601a-601d of the continuous suture thread 500. The double knot 601a is formed by a loop of suture thread passing out of the graft material 21 and then back into the graft material at the same side of the stent strut 351 and from the other side of graft material passes back out again on the opposite side of the strut 351, to be looped underneath the first formed loop, over the stent strut 351, to enter into the other side of the graft material on the first side of the strut, then looped out again at the other side of the strut and then passed through the formed second loop on the first side of the strut, before passing towards the second double loop arrangement. FIG. 7B shows one of the double-loop knots depicted in schematic form in FIG. 7A.

Figure 8:
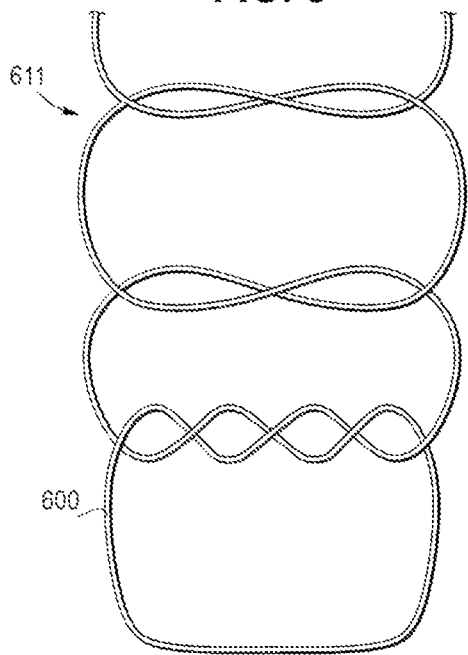
FIG. 8 is a schematic view similar to that of FIG. 5, showing another embodiment of locking knot of the tightened suture of the embodiment of FIG. 7A.

Referring to FIG. 8, a proximal sutured knot 611 is shown in more detail. Similar to the embodiment of FIGS. 5 and 6A, the proximal sutured knot 611 secures an apex 311 to the graft 20 with a locking knot formed by two pairs of double knots, sometimes referred to as reef knots. This provides a staggered stitch with, for each double knot, a double formed left over right stitch, as can be seen in FIG. 8. The staggered stitch is fast to sew and reduces the number of times the manufacturer has to swap tools to complete the sewing process. This can help with cross-contamination from handling tools too often and requires less time to be spent handling the graft during manufacture thereof.

Figure 9A:
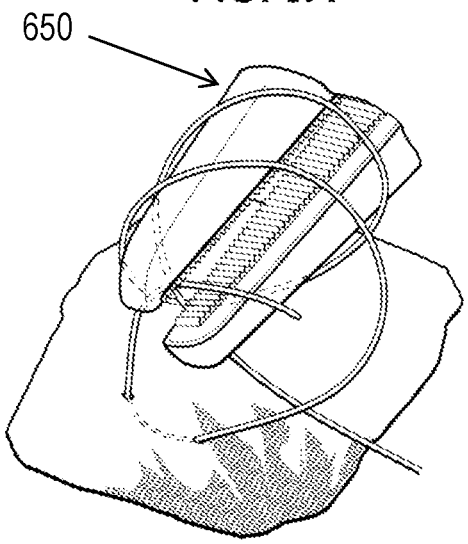
FIGS. 9A to 9C are schematic diagrams showing a method of forming the suture arrangement of FIGS. 7 and 8.
Figure 9B:
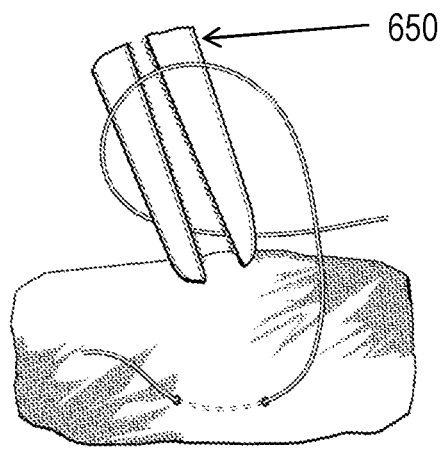
Figure 9C:
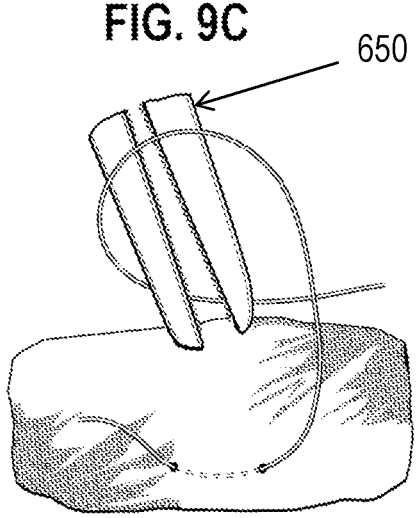

Referring now to FIGS. 9A to 9C, these depict how the double knot arrangement of FIGS. 7A to 8 can be achieved in one manufacturing implementation. With reference to FIG. 9A, the first knot is looped twice around needle holders 650 and tightened. With reference to FIG. 9B, the second knot is looped once around the needle holders 650 and tightened, while, with reference to FIG. 9C, the third knot is looped once around the needle holders 650 and tightened. Thereafter, the suture tails are cut with a finishing length of, preferably, around 3.0 mm plus or minus 1.0 mm.

Figure 10:
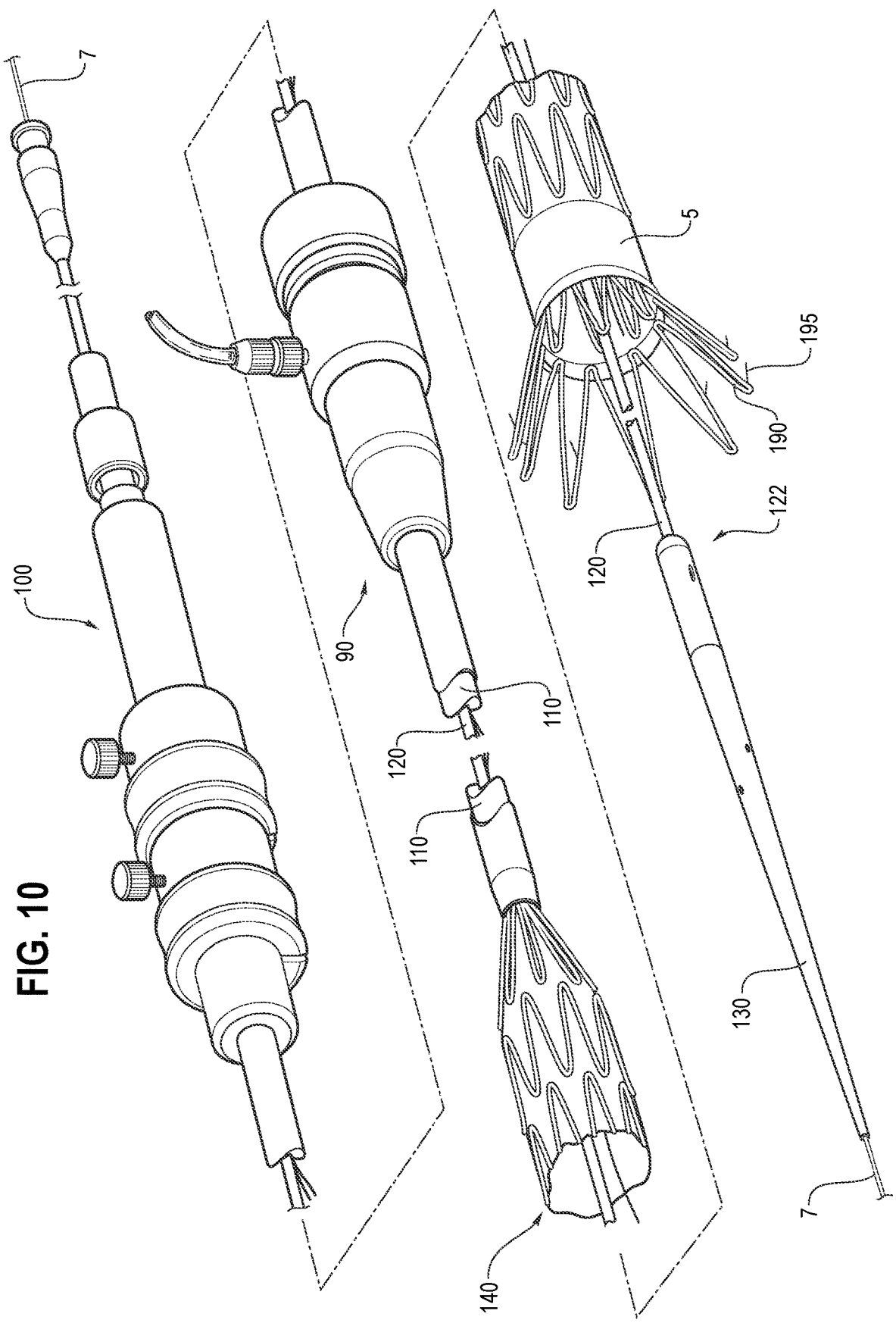
FIG. 10 shows a stent-graft according to the invention being deployed from a delivery device.

Turning now to FIG. 10, a delivery assembly 100 sliding along a guide wire 7 and having an introducer 90 is shown. Such a delivery assembly 100 can be used to deliver a stent-graft according to the teachings herein. The delivery assembly 100 comprises a guide wire catheter 120 having a tip 130 mounted to a proximal end 122 thereof. A distal delivery member 110, which could be referred to as a pusher, is mounted around the guide wire catheter 120 and is located distal of the tip 130. A stent-graft receiving portion 140 is provided between the tip 130 and the distal delivery member 110. The delivery assembly 100 is slidably mounted through the introducer 90. A handle 150 is manipulable to slide the distal delivery member (pusher) 110 through the introducer 90 so as to position the stent-graft 5 in the vascular system of a patient.

Figure 11A:
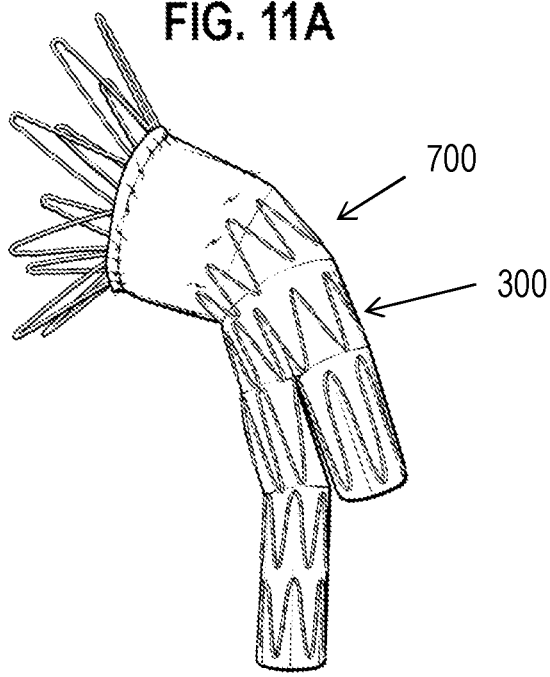
FIGS. 11A and 11B an example of branched stent graft in a curved in-use configuration and a straight configuration, respectively.
Figure 11B:
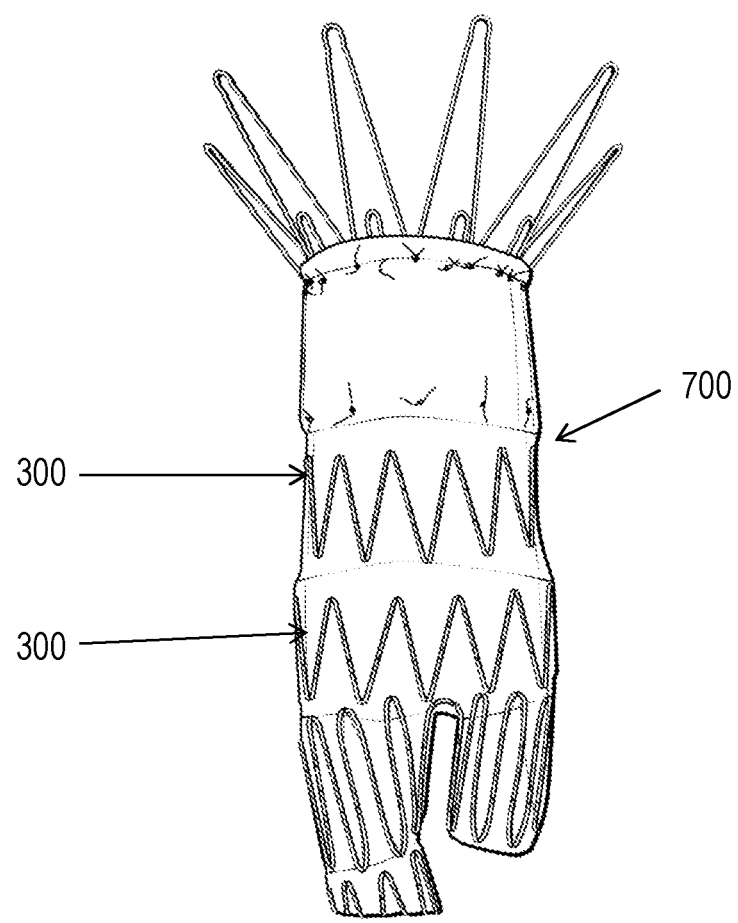
Figure 12:
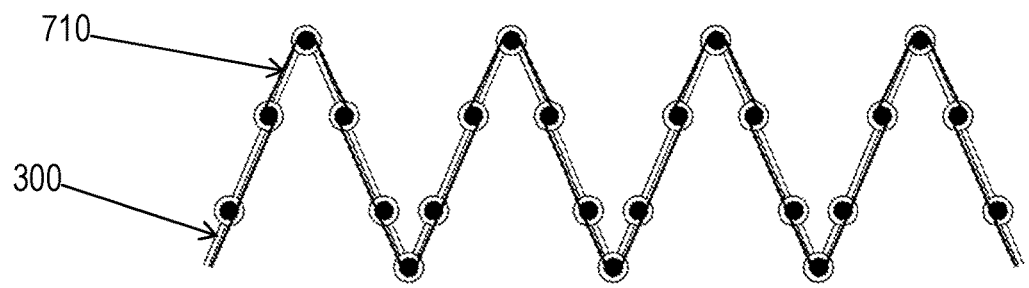
FIG. 12 is a schematic diagram of a prior art suture stent fixation arrangement.

FIGS. 11A and 11B show a stent graft having a plurality of stents 300 attached to the graft material in a conventional manner, as shown in FIG. 12, that is with a running suture 700 extending along each strut of the stent and to each apex. The stent is firmly attached, which results in stiffness of the stent graft 700 to bending, as will be apparent from FIG. 11A and as is known in the art.

Figure 13A:
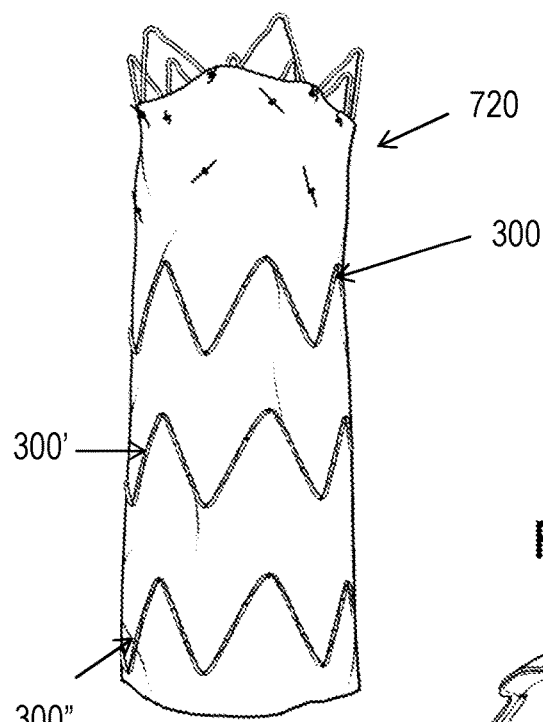
FIGS. 13A to 13C show a stent graft having a sutured stent according to FIG. 12 will curve in use.
Figure 13B:
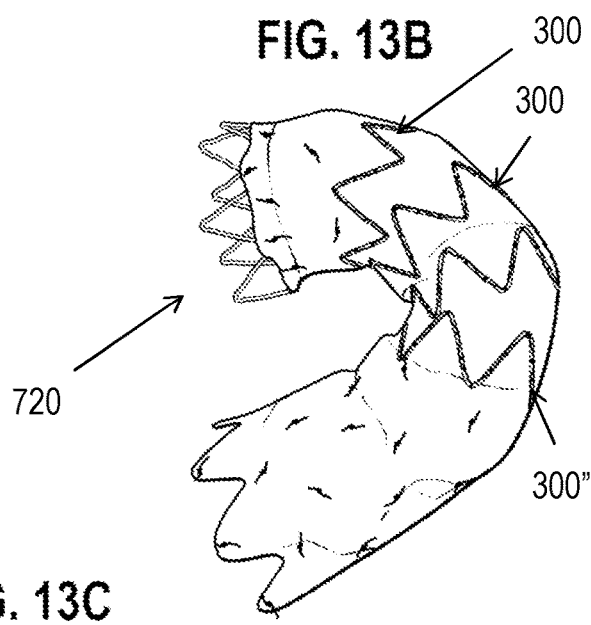
Figure 13C:
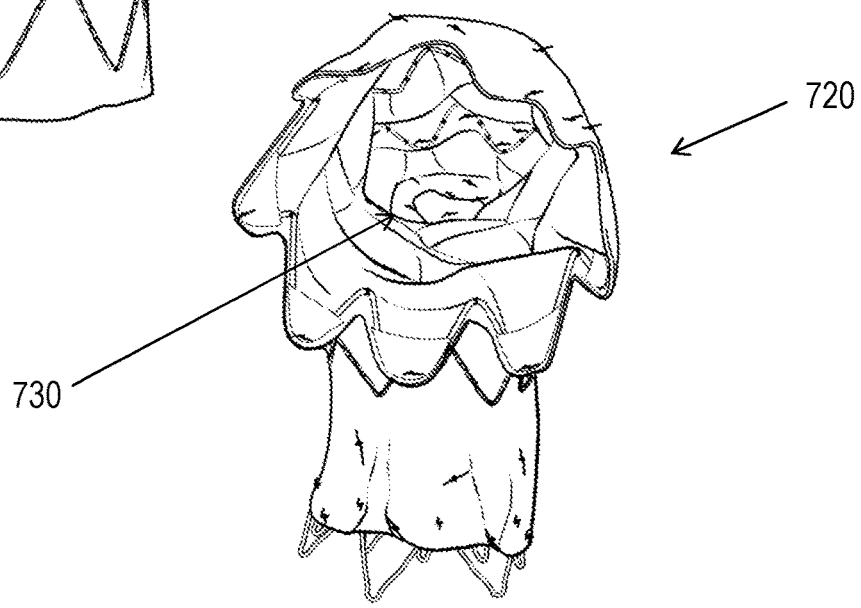

Referring now to FIGS. 13A to 13B, these show another embodiment of stent graft 720 that again has the stents attached to the graft material by a running suture that extends along the entirety of each strut to the apices thereof. The stents in this example are spaced form one another by around 10 millimetres. As can be seen in particular in FIGS. 13B and 13C, while the stent spacing allows greater bending of the stent graft compared to the example of FIGS. 11A and 11B, when curved at a relatively tight angle, as might occur for example in the aortic arch, significant ruffling 730 of the graft material occurs particularly at the inside of the curve. This ruffling can cause significant turbulence in the flow of fluid (blood) through the stent graft, disrupting normal blood flow and function.

Referring now to FIG. 14, this shows in schematic form another embodiment of stent attachment arrangement similar to that of FIG. 2 but in which the stent apices 411-414 and 481-485 do not have any sutures attaching them to the graft material. In other words, the stent 300 is attached to the graft tubing solely by the intermediate running suture 500. This may be achieved by use of tack knots that may be removed, degrade or by omitting them entirely. In other embodiments, only loose tack knots may be used that allow sliding of the stent within the constraints of the intermediate running suture.

While the embodiment of FIG. 14 shows neither the proximal nor the distal apices 411-414 and 481-485 having any tack knots, in practice it may be preferred to maintain the proximal tack knots and remove the distal tack knots.

Referring now to FIGS. 14A to 14C, this shows an embodiment similar to that of FIG. 14 but in which the proximal bridging portions 530 are disposed inside the graft tubing, which is an alternative to the arrangement shown in FIG. 14. In practice, the bridging portions 530, 540 may weave into and out of the graft material so as in effect to be held by the material. The intermediate suture arrangement assist in the control of the graft material as the stent graft 10 is curved, as it would be in a curved vessel, and in particular prevents or substantially limits ruffling of graft material at the interior of the curve, as can be seen by a comparison of FIG. 14C with FIG. 13C.

Figure 15:
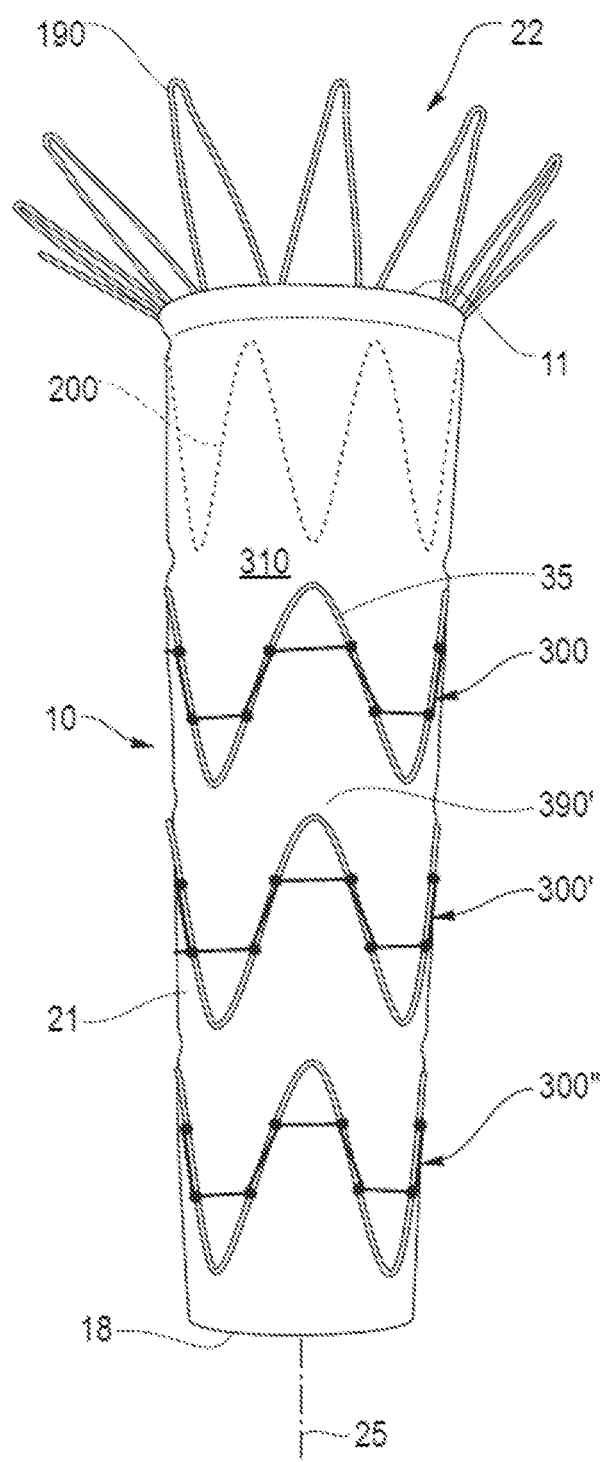
FIG. 15 is a schematic diagram of a stent graft with stents attached to the graft according to the teachings herein.

FIG. 15 shows a stent graft provided with three stents 300, 300' and 300" having the intermediate suture arrangement of FIG. 14 and free, that is non attached, stent apices.

Figure 16:
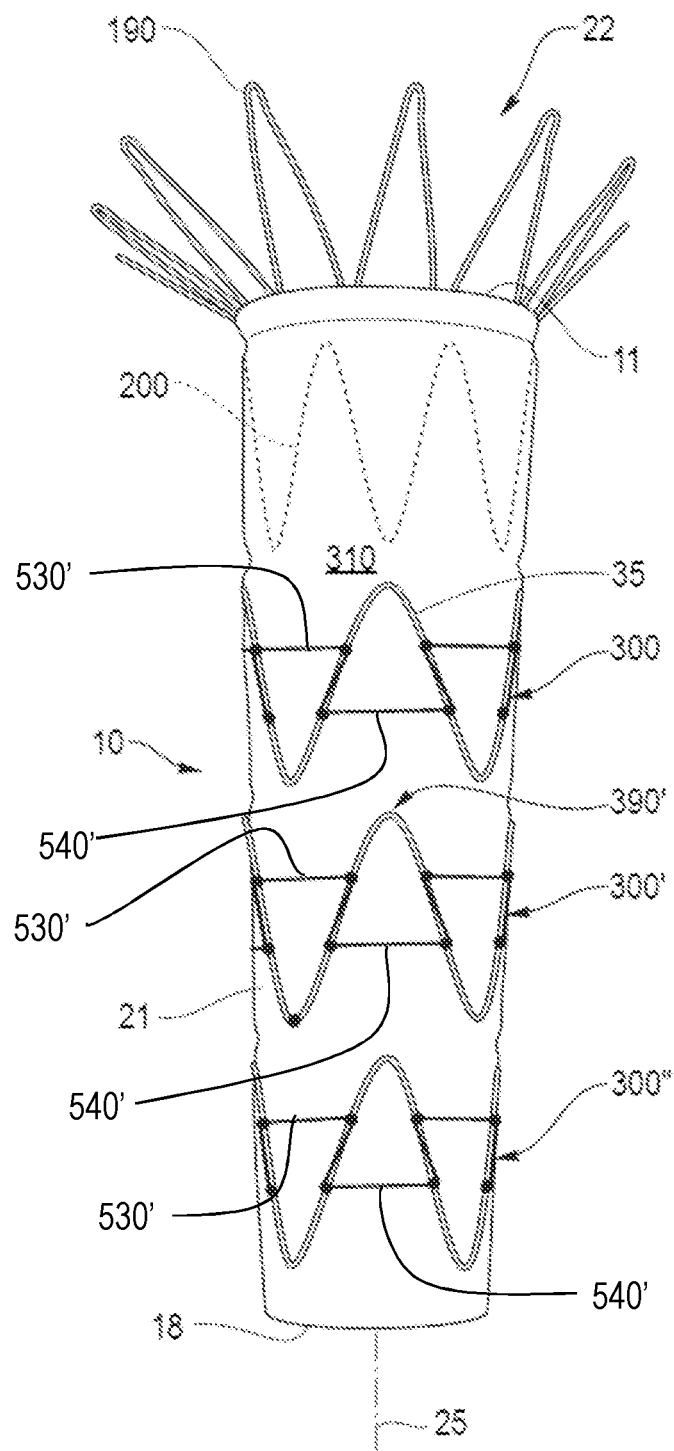
FIG. 16 is a schematic diagram of another embodiment of stent graft with stents attached to the graft according to the teachings herein.

FIG. 16 shows a slightly modified embodiment, in which the bridging portions 530' and 540' are arranged between adjacent apices of the stents 300, 300', 300", that is at the wider ends of the V formed by adjacent struts of the stent.

Preferably, the graft 20 is formed from tube material may be formed from a biocompatible material that is substantially non-toxic in the in vivo environment of its intended use and will be substantially not rejected by the patient's physiological system (i.e., is non-antigenic). For example, the graft tube material may be made of an expanded polytetrafluoroethylene (ePTFE), polytetrafluoroethylene, silicone, polyurethane, polyamide (nylon), polyethylene, polypropylene, polyaramids, polyacrylonitrile, cellulose, or another flexible biocompatible material. The graft tube material also may be made of known fabric graft materials, e.g., woven polyester such as DACRON® from Invista (Wichita, Kans.), polyetherurethanes such as THORALON® from Thoratec Corporation (Pleasanton, Calif.), or polyethylene such as an ultra-high molecular weight polyethylene (UHMwPE) such as DYNEEMA® from DSM Dyneema LLC (Stanley, N.C.). In addition, materials that are not inherently biocompatible may be subjected to surface modifications to render the materials biocompatible. Examples of surface modifications include, for example, graft polymerization of biocompatible polymers on the surface, coating of the surface with a crosslinked biocompatible polymer, chemical modification with biocompatible functional groups, or immobilization of a compatibilizing agent such as heparin or other biocompatible substances. Thus, any fibrous material having sufficient strength to survive in the in vivo environment may be used to form a textile graft, provided the final textile is biocompatible.

The graft tube material may also include a bio-remodelable material such as reconstituted or naturally-derived collagenous materials. Suitable remodelable materials can be provided by collagenous extracellular matrix (ECM) materials possessing biotropic properties. For example, suitable collagenous materials may include ECM materials such as those comprising submucosa, renal capsule membrane, dermal collagen, dura mater, pericardium, fascia lata, serosa, peritoneum or basement membrane layers, including liver basement membrane. Suitable submucosa materials for these purposes may include, for instance, intestinal submucosa including small intestinal submucosa, stomach submucosa, urinary bladder submucosa and uterine submucosa. Collagenous matrices including submucosa (potentially along with other associated tissues) useful in the present invention can be obtained by harvesting such tissue sources and delaminating the submucosa-containing matrix from smooth muscle layers, mucosal layers, and/or other layers occurring in the tissue source. For additional information as to some of the materials useful in the present invention, and their isolation and treatment, reference can be made, for example, to U.S. Pat. Nos. 4,902,508, 5,554,389, 5,993,844, 6,206,931, and 6,099,567. A non limiting example of a suitable remodelable material may include SURGISISR™ BIODESIGN™ from Cook Medical (Bloomington, Ind.) or the graft prosthesis material described in U.S. Pat. No. 6,206,931 to Cook et al., which is incorporated herein by reference in its entirety. The graft tube material also may be made of any of the materials described in U.S. Pat. No. 7,407,509 to Greenberg et al. or U.S. Patent Application Publication Number 2009/0171451 to Kuppurathanam et al., which are incorporated herein by reference in their entirety.

The stents of the embodiments of the invention, such as stents 200, 300, 300' and 300", may have any suitable stent pattern known in the art. The stents may be balloon expandable. Preferably, the stents may be self-expandable. The stents can maintain the patency of the prosthesis and ensure adequate sealing against the surrounding vascular tissue. One goal for stent design and placement, whether internal or external, may be to prevent metal-to-metal contact points, prevent contact between two different types of alloys, and minimize micro-motion. The arrangement shown in FIG. 1, where adjacent stents are positioned such that peaks from one of the plurality of external stents extend towards the valleys of another of the plurality of external stents, assist in preventing metal-to-metal contact points. Stent sizing, spacing, and design may be determined so that there is no stent-to-stent contact even in tortuous anatomy. Stents preferably may be placed to maximize prosthesis flexibility while maintaining patency, as well as reduce material wear and stent fatigue. Furthermore, it is preferable that the stents do not interfere with the branch, that they minimize the potential for galvanic corrosion and ensure adequate joint stability. Stent amplitude, spacing, and stagger preferably may be optimized for each prosthesis design. Any of the stents mentioned herein may have barbs and/or other anchoring members to help decrease prosthesis migration.

One example of a stent pattern is the Z-stent or Gianturco stent design. Each Z-stent may include a series of substantially straight segments or struts interconnected by a series of bent segments or bends. The bent segments may include acute bends or apices. The Z-stents are arranged in a zig zag configuration in which the straight segments are set at angles relative to one another and are connected by the bent segments. This design provides both significant radial force as well as longitudinal support. In tortuous anatomy, branches or fenestrations, it may be preferable to use alternative stents or modifications to the Z-stent design to avoid stent-to-stent contact. Alternative stents may include, for example, annular or helical stents. Furthermore, in complex anatomical situations, external stents may have the potential to become intertwined with the wires or other devices utilized to ensure branch vessel access, sealing, and fixation. Thus, in some instances, it may be desirable to affix some of the stents to the internal surface of the prosthesis.

The stents described herein may be made from any suitable material known in the art. In one example, the stents may be made from standard medical grade stainless steel and are soldered using silver standard solder (0 lead/0 tin). In other examples, the stents may be made from a metallic material selected from any type of stainless steel, silver, platinum, palladium, gold, titanium, tantalum, iridium, tungsten, cobalt, chromium, cobalt-chromium alloy 1058, cobalt-based 35N alloy, nickel-based alloy 625, a molybdenum alloy, a molybdenum alloy including about 0.4% to about 0.8% of lanthanum oxide (Li.sub.20.sub.3), and a nickel-titanium alloy, or other suitable materials known in the art. The stents also may be made from nitinol or other shape-memory metal. Moreover, the stents may be configured in a variety of ways to provide a suitable intraluminal support structure. For example, one or more stents may be made from a woven wire structure, a laser-cut cannula, individual interconnected rings, or another pattern or design.

Stent-grafts according to the teachings herein, such as stent-graft 10, can be made efficiently. They do not require temporary stitches that are used commonly in producing other stent-grafts, particularly those having external stents. This saves considerable time and improves manufacturing efficiency. It is also easier to construct as the sewer does not have to turn the graft upside down continuously as they sew along the strut. Instead, the graft can be held in one position (upright) as the suture runs along the graft. Making the process easier reduces errors and the need for re-work.

Aside from being more efficient, avoiding the need for temporary or tacking stitches avoids additional holes being formed in the graft material. Also avoided is the potential for tacking stitches to be missed and then forming a bio-burden with the patient during or after endovascular surgery.

Stent-grafts according to the teachings herein, such as stent-graft 10, provide a safer prosthetic in that cuts to the graft material are much less likely than stent-grafts that utilise temporary stitches (for instance to initially hold apices in place). Avoiding cuts and holes is important because cuts or holes can cause blood leakage into aneurysmal or other areas outside the lumen of the vessel being repaired.

A method of forming an endoluminal prosthetic device, such as is shown in FIGS. 1 and 2, will now be described.

A graft comprising a bio-compatible material, such as the bio-compatible material described above, defining a main tubular body is provided. A first external stent is also provided, the first external stent comprising a plurality of struts and apices between the struts, the apices including proximal apices and distal apices. The first stent 300 is positioned around the main tubular body (such as is shown in FIGS. 1 and 2). The proximal apices and the distal apices of the first stent are joined to the graft using respective sutured proximal knots and sutured distal knots. The struts of the first stent are joined to the graft by intermediate sutured knots in a continuous suture, the continuous suture ridging between neighbouring struts of the stent, as is clearly shown in FIG. 2.

In one embodiment of a method according to the invention, the step of joining the proximal and distal apices of the first stent to the graft comprises using locking knots, such as the locking knot shown in FIG. 5.

In a further method according to the invention, the step of joining the struts of the first stent to the grafts by knots in a continuous suture comprises passing the continuous suture into and out of the graft, such as is shown in FIG. 3A.

It is preferred that the intermediate suture 500 that provides the bridging portions 530, 540 is a continuous suture that extends circumferentially around the entirety of the stent 300, 300', 300". This reduces the number of tie knots, optimises compressibility of the stent graft for deployment and facilitates assembly. However, in some embodiments the running intermediate suture 500 may be provided in a plurality of lengths, that is each would extend only partially around the stent 300, 300', 300". It is also possible to have the intermediate sutures 500 as individual bridging portions 530, 540 with the suture tied and terminating at each end of a bridging portion, although this is a less preferred arrangement.

As explained above, one or more or all of the stents 300,300', 300", that is the stents provided with intermediate bridging sutures, could be disposed on the outside of the graft tubing, as in the preferred embodiments described above and shown in the drawings or one or more could be disposed inside the graft tubing.

Throughout this specification and the claims that follow unless the context requires otherwise, the words 'comprise' and 'include' and variations such as 'comprising' and 'including' will be understood to imply the inclusion of a stated integer or group of integers but not the exclusion of any other integer or group of integers.

The reference to any prior art in this specification is not, and should not be taken as, an acknowledgement of any form of suggestion that such prior art forms part of the common general knowledge.

It will be appreciated by those skilled in the art that the invention is not restricted in its use to the particular application described or to stent grafts per se, being applicable to other types of implantable medical devices having a stent or scaffold attached to a support such as a graft material or other membrane. Neither is the present invention restricted in its preferred embodiment with regard to the particular elements and/or features described or depicted herein. It will be appreciated that the invention is not limited to the embodiment or embodiments disclosed, but is capable of numerous rearrangements, modifications and substitutions without departing from the scope of the invention as set forth and defined by the following claims.

The invention claimed is:

1. A stent-graft comprising:
   a graft having a proximal end and a distal end and defining an elongate lumen having a longitudinal axis;
   an internal sealing stent adjacent the proximal end of the graft;
   a plurality of body stents distal of the internal sealing stent, the plurality of body stents having a plurality of struts and an apex between each of the plurality struts, the apices including proximal apices and distal apices;
   at least one running suture attaching a body stent of plurality of body stents to the graft, the running suture comprising:
      first and second knots knotted along a length of the struts of the plurality of struts at intermediate points spaced from the proximal and distal apices, wherein a length of the running suture runs between the first and second knots; and
      at least one bridging portion spaced from the proximal and distal apices and more proximate the distal apices, the at least one bridging portion extending transversely between the first knot on a first strut and a first knot on a second strut next adjacent the first strut and linking the first knot on the first strut and the first knot on the second strut.

2. The stent-graft of claim 1, wherein the at least one bridging portion comprises a plurality of bridging portions.

3. The stent graft of claim 2, wherein each of the plurality of bridging portions extends transversely between two struts of a distal apex.

4. The stent graft of claim 2, wherein each of the bridging portions extends between a first strut of a first distal apex and a first strut of a second distal apex.

5. The stent graft of claim 1, wherein a length of the at least one bridging portion passes in and out of the graft between next adjacent struts.

6. The stent graft of claim 1, further comprising a series of proximal tack knots securing the one or more of the proximal apices of the at least one body stent to the graft.

7. The stent graft of claim 1, further comprising a series of distal tack knots securing one or more of the distal apices of the at least one body stent to the graft.

8. The stent graft of claim 7, wherein the series of distal tack knots are configured such that the at least one body stent can slide relative to the graft.

9. The stent graft of claim 1, further comprising a third knot in the running suture between each of the first and second knots.

10. The stent-graft of claim 1, wherein the bridging portions are disposed transverse to the longitudinal axis of the lumen.

11. The stent graft of claim 1, wherein each strut of the plurality of struts has a first knot and a second knot and a first bridging portion extending from the first knot and a second bridging portion extending from the second knot.

12. The stent-graft of claimed claim 1, wherein the at least one running suture is a single continuous length of suture.

13. The stent-graft of claim 1, wherein each of the plurality of body stents is attached to the graft by a running suture of the at least one running suture.

14. A stent-graft comprising:
a graft defining an elongate lumen having a longitudinal axis;
a proximal inflow end;
a distal outflow end;
a plurality of ring stents having a plurality of struts and apices between the struts, the apices including proximal apices and distal apices;
running sutures attaching a plurality of the plurality of ring stents to the graft, each running suture comprising:
at least first and second knots knotted along the length of each strut at intermediate points on the struts away from the proximal and distal apices;
a length of running suture running between the first and a second knots on each strut; and
a first bridging portion adjacent a first distal apex and extending transversely between a first knot of the running suture on a first strut and a first knot of the running suture on a second strut adjacent the first strut; and
a second bridging portion adjacent a second distal apex and extending transversely between a first knot on a third strut to a first knot on a fourth strut adjacent the third strut;
wherein the first bridging portion and the second bridging portion are disposed more proximate to the first and second distal apices.

15. The stent graft of claim 14, wherein at least a portion of the first and second bridging portions passes through the graft.

16. The stent graft of claim 14, wherein the running suture is continuous about a circumference of at least one ring stent of the plurality of ring stents.

17. A stent-graft comprising:
a graft defining an elongate lumen having a longitudinal axis;
a proximal inflow end;
a distal outflow end;
at least one stent having a plurality of struts and an apex between each of the plurality struts, the apices including proximal apices and distal apices;
a running suture attaching the at least one stent to the graft, the running suture comprising:
first and second knots knotted along a length of at least one strut of the plurality of struts at intermediate points spaced from the proximal and distal apices;
a length of running suture between the first and second knots; and
a first bridging portion extending between a first knot on a first strut and a first knot on a second strut next adjacent the first strut, and a second bridging portion extending from a first knot on a third strut to a first knot of a fourth strut next adjacent the second strut;
wherein the running suture is a single continuous length of suture; and
wherein the first bridging portion and the second bridging portion are disposed more proximate to the first and second distal apices.

18. The stent-graft of claim 17, wherein the at least one stent comprises a plurality of stents each attached to the graft by a running suture.

19. The stent graft of claim 17, wherein the first bridging portion extends between extends between two struts of a distal apex.

20. The stent graft of claim 17, wherein a length of the bridging portions passes in and out of the graft between next adjacent struts.

* * * * *